(12) United States Patent
Kensil

(10) Patent No.: US 7,858,589 B2
(45) Date of Patent: Dec. 28, 2010

(54) COMPOSITIONS OF CPG AND SAPONIN ADJUVANTS AND USES THEREOF

(75) Inventor: Charlotte A. Kensil, Milford, MA (US)

(73) Assignee: Antigenics Inc., Lexington, MA (US)

( * ) Notice: Subject to any disclaimer, the term of this patent is extended or adjusted under 35 U.S.C. 154(b) by 946 days.

(21) Appl. No.: 11/373,806

(22) Filed: Mar. 10, 2006

(65) Prior Publication Data

US 2006/0177458 A1 Aug. 10, 2006

Related U.S. Application Data

(62) Division of application No. 09/369,941, filed on Aug. 6, 1999, now Pat. No. 7,049,302.

(60) Provisional application No. 60/128,608, filed on Apr. 8, 1999, provisional application No. 60/095,913, filed on Aug. 10, 1998.

(51) Int. Cl.
  A61K 39/00 (2006.01)
  A61K 39/38 (2006.01)
  A61K 45/00 (2006.01)
  A61K 47/00 (2006.01)
  A61K 31/70 (2006.01)
  A01N 43/04 (2006.01)

(52) U.S. Cl. ................ 514/44 R; 424/184.1; 424/278.1

(58) Field of Classification Search ........................ None
  See application file for complete search history.

(56) References Cited

U.S. PATENT DOCUMENTS

| | | | |
|---|---|---|---|
| 4,469,863 A | 9/1984 | Ts'o et al. | |
| 4,522,811 A | 6/1985 | Eppstein et al. | |
| 5,023,243 A | 6/1991 | Tullis | |
| 5,057,540 A * | 10/1991 | Kensil et al. | 424/278.1 |
| 5,273,965 A * | 12/1993 | Kensil et al. | 514/3 |
| 5,352,449 A * | 10/1994 | Beltz et al. | 424/187.1 |
| 5,443,829 A * | 8/1995 | Kensil et al. | 424/765 |
| 5,583,112 A * | 12/1996 | Kensil et al. | 514/25 |
| 5,650,398 A * | 7/1997 | Kensil et al. | 514/25 |
| 5,808,024 A | 9/1998 | Sasaki et al. | |
| 5,968,909 A | 10/1999 | Agrawal et al. | |
| 5,977,081 A | 11/1999 | Marcianai | |
| 6,013,258 A | 1/2000 | Urban et al. | |
| 6,207,646 B1 * | 3/2001 | Krieg et al. | 514/44 |
| 6,214,806 B1 * | 4/2001 | Krieg et al. | 514/44 |
| 6,218,371 B1 * | 4/2001 | Krieg et al. | 514/44 |
| 6,231,859 B1 * | 5/2001 | Kensil | 424/184.1 |
| 6,239,116 B1 * | 5/2001 | Krieg et al. | 514/44 |
| 6,406,705 B1 | 6/2002 | Davis et al. | |
| 6,429,199 B1 * | 8/2002 | Krieg et al. | 514/44 |
| 6,524,584 B2 | 2/2003 | Kensil | |
| 6,544,518 B1 * | 4/2003 | Friede et al. | 424/184.1 |
| 6,558,670 B1 * | 5/2003 | Friede et al. | 424/184.1 |
| 6,645,495 B1 | 11/2003 | Kensil et al. | |
| 7,049,302 B1 * | 5/2006 | Kensil | 514/44 |
| 7,399,472 B2 * | 7/2008 | Friede et al. | 424/184.1 |
| 7,488,490 B2 * | 2/2009 | Davis et al. | 424/278.1 |
| 7,550,145 B2 * | 6/2009 | O'Hagan et al. | 424/184.1 |
| 2001/0034330 A1 | 10/2001 | Kensil et al. | |
| 2002/0164341 A1 * | 11/2002 | Davis et al. | 424/184.1 |
| 2003/0091599 A1 | 5/2003 | Davis et al. | |
| 2003/0161834 A1 | 8/2003 | Friede et al. | |
| 2003/0224010 A1 * | 12/2003 | Davis et al. | 424/185.1 |
| 2006/0177458 A1 * | 8/2006 | Kensil | 424/184.1 |
| 2006/0239963 A1 * | 10/2006 | Morein et al. | 424/85.1 |
| 2008/0311156 A1 * | 12/2008 | Friede et al. | 424/208.1 |
| 2009/0047306 A1 * | 2/2009 | Nash et al. | 424/204.1 |

FOREIGN PATENT DOCUMENTS

| | | |
|---|---|---|
| BE | 9908885 | 4/1999 |
| EP | 1005368 | 6/2000 |
| JP | 2001503267 | * 3/2001 |
| JP | 2001513776 | * 9/2001 |
| WO | WO 95/08350 A1 * | 3/1995 |
| WO | WO 95/26204 | 10/1995 |
| WO | WO 96/11711 | 4/1996 |
| WO | WO 96/38161 | 12/1996 |
| WO | WO 98/18810 | 5/1998 |
| WO | WO 98/37919 | 9/1998 |
| WO | WO 98/40100 | 9/1998 |
| WO | WO 98/52581 A1 * | 11/1998 |
| WO | WO 98/55495 | 12/1998 |
| WO | WO 99/58118 | 11/1999 |
| WO | WO 99/61056 | 12/1999 |

(Continued)

OTHER PUBLICATIONS

Rafi-Janajreh et al, Experimental Parasitology, 2002, 101:3-12.*

(Continued)

*Primary Examiner*—N. M Minnifield
(74) *Attorney, Agent, or Firm*—Jones Day

(57) ABSTRACT

Vaccine compositions of immunostimulatory oligonucleotides and saponin adjuvants and antigens and the use thereof for stimulating immunity, enhancing cell-mediated immunity, and enhancing antibody production are disclosed. Also described are immune adjuvant compositions comprising immunostimulatory oligonucleotides and saponin adjuvants, as well as methods for increasing an immune response using the same.

65 Claims, 9 Drawing Sheets

FOREIGN PATENT DOCUMENTS

| | | |
|---|---|---|
| WO | WO 99/62923 | 12/1999 |
| WO | WO 00/21556 | 4/2000 |
| WO | WO 00/62800 | 10/2000 |
| WO | WO 02/32450 | 4/2002 |
| WO | WO 03/026688 A1 * | 4/2003 |
| WO | WO 03/030934 * | 4/2003 |
| WO | WO 03/039595 A1 * | 5/2003 |
| WO | WO 03/094963 A1 * | 11/2003 |

OTHER PUBLICATIONS

Singh et al, Nature Biotechnology, Nov. 1999, 17:1075-1081.*
Qiao et al, Hepatology, 2003, 37:52-59.*
Kensil, In: Immunopotentiators in Modern Vaccines, ed. Virgil et al, 2006, pp. 109-122.*
McCluskie et al, Current Drug Targets—Infectious Disorders, 2001, 1:263-271.*
Pichichero, Human Vaccines, Jul./Aug. 2008, 4/4:262-270.*
Fraser et al, Expert Rev. Vaccines, 2007, 6/4:559-578.*
Kensil et al, Frontiers in Bioscience, Sep. 1, 2004, 9:2972-2988.*
Krieg et al, Trends in Microbiology, Jun. 2001, 9/8:249-252.*
Verthelyi et al, Clinical Immunology, 2003, 109:64-71.*
Lin et al, J. Invest. Medicine, Sep. 1997, 45/7:333A (abstract only).*
Yamamoto et al, Antisense Research and Development, 1994, 4:119-122.*
Krieg et al, Immunology Today, 2000, 21/10:521-526.*
McCluskie et al, Mol. Med., 1999, 5/5:287-300.*
Ballas et al., 1996, "Induction of NK activity in murine and human cells by CpG motifs in oligodeoxynucleotides and bacterial DNA," J. Immunol. 157:1840-1845.
Cowdery et al., 1996, "Bacterial DNA induces NK cells to produce IFN-gamma in vivo and increases the toxicity of lipopolysaccharides," J. Immunol. 156:4570-1475.
Krieg et al., 1996, "CpG motifs in bacterial DNA trigger direct B-cell activation," Nature 374:546-549.
Declaration of Charlotte Kensil under 37 CFR § 1.132, dated Apr. 23, 2004, of U.S. Appl. No. 09/369,941.
Office Action, dated Jan. 18, 2001, of U.S. Appl. No. 09/369,941.
Office Action, dated Mar. 14, 2002, of U.S. Appl. No. 09/369,941.
Advisory Action, dated Sep. 26, 2002, of U.S. Application No. 09/369,941.
Office Action, dated Jan. 31, 2003, of U.S. Application No. 09/369,941.
Office Action, dated Oct. 27, 2003, of U.S. Application No. 09/369,941.
Advisory Action and Examiner Interview Summary Record, dated Apr. 28, 2004, of U.S. Appl. No. 09/369,941.
Office Action, dated Mar. 2, 2005, of U.S. Appl. No. 09/369,941.
Examiner Interview Summary Record, dated Jul. 6, 2005, of U.S. Appl. No. 09/369,941.
Examiner Interview Summary Record, dated Nov. 17, 2005, of U.S. Appl. No. 09/369,941.
Agrawal et al., Oligodeoxynucleoside phosphoramidates and phosphorothioates as inhibitors of human immunodeficiency virus. Proc Natl Acad Sci USA. 1988, 85(19):7079-7083.
Agrawal S., Antisense oligonucleotides as antiviral agents. Trends Biotechnol. 1992, 10(5):152-158.
Beaucage et al., Deoxynucleotide phosphoramidites—A new class of key intermediates for deoxypolynucleotide synthesis. Tet. Let. 1981, 22:1859-1862.
Boggs et al., Characterization and modulation of immune stimulation by modified oligonucleotides. Antisense Nucleic Acid Drug Dev. 1997, 7(5):461-471.
Campbell & Peerbaye, Saponin. Res. Immuno. 1992, 143:526-530.
Carson et al., Oligonucleotide adjuvants for T helper 1 (Th1)-specific vaccination. J. Exp. Med. 1997, 186(10):1621-1622.
Chavali & Campbell, Immunomodulatory Effects of Orally-Administered Saponins and Nonspecific Resistance Against Rabies Infection. Int. Archs. Allergy Appl. Immun. 1987, 84:129-134.
Chavali et al., Immunopotentiation by Orally-Administered Quillaja Saponins: Effects in Mice Vaccinated Intraperitoneally Against Rabies, Clin Exp. Immunol. 1988, 74:339-343.
Chavali et al., An In Vitro Study of Immunomodulatory Effects of Some Saponins. Int. J. Immunopharmac. 1987, 9(6):675-683.
Dalsgaard, K. A study of the isolation and characterization of the saponin quil a. Acta Veterinia Scandinavica 1978, 69:1-40.
Elkins et al., Bacterial DNA containing CpG motifs stimulates lymphocyte-dependent protection of mice against lethal infection with intracellular bacteria. J Immunol. 1999, 162(4):2291-2298.
Froehler B, Deoxynucleoside H-Phosphate diester intermediates in the synthesis of internucleotide phosphate analogues. Tet. Let. 1986, 27:5575.
Froehler et al., Synthesis of DNA via deoxynucleoside H-phosphonate intermediates. Nucleic Acids Res. 1986, 14(13):5399-5407.
Gaffney et al., Large-scale oligonucleotide synthesis by the H-Phosphonate method. Tet. Let. 1988, 29:2619-2622.
Garegg et al., Nucleoside H-phosphonates III. Chemical synthesis of oligodeoxyribonucleotides by the hydrogenphosphonate approach. Tet. Let. 1986, 27:4051-4054.
Garegg et al., Nucleoside H-phosphonates IV. Automated solid phase synthesis of oligoribonucleotides by the hydrogenphosphonate approach. Tet. Let. 1986, 27:4055-4058.
Goodchild J. Conjugates of oligonucleotides and modified oligonucleotides: a review of their synthesis and properties. Bioconjugate Chem. 1990, 1:165.
Higuchi et al., Structure of desacylsaponins obtained from the bark of Quillaja saponaria. Phytochemistry 26:229-235, 1987.
Kensil et al., Structure/Function relationship in adjuvants from Quillaja saponaria Molina. Vaccine 92 (Cold Spring Harbor Laboratory Press) 1992,pp. 35-40.
Kim et al., Effect of immunological adjuvant combinations on the antibody and T-cell response to vaccination with MUCI-KLH and GD3-KLH conjugates. Vaccine. 2001, 19(4-5):530-537.
Kirby et al., Effects of anticholinesterase drugs tacrine and E2020, the 5-HT3 antagonist ondansetron, and the H3 antagonist thioperamide, in models of cognition and cholinergic function. Behav Pharmacol. Nov. 1996;7(6):513-525.
Klinman et al., CpG motifs present in bacteria DNA rapidly induce lymphocytes to secrete interleukin 6, interleukin 12, and interferon gamma. Proc Natl Acad Sci USA. 1996, 93(7):2879-2883.
Krieg et al., Oligodeoxynucleotide modifications determine the magnitude of B cell stimulation by CpG motifs. Antisense Nucleic Acid Drug Dev. 1996, 6(2):133-139.
Krieg et al., CpG DNA induces sustained IL-12 expression in vivo and resistance to Listeria monocytogenes challenge. J. Immunol. 1998, 161(5):2428-2434.
Lipkin, "Vegemania: Scientist Tout the Health Benefits of Saponins", Science News, 1995, 148:392-393.
Maharaj et al., Immune Responses of Mice to Inactivated Rabies Vaccine Administered Orally: Potentiation by Quillaja Saponin, Can. J. Microbiol. 1986, 32:414-420.
Marciani et al., Genetically-engineered subunit vaccine against feline leukemia virus: protective immune response in cats. Vaccine. 1991, 9(2):89-96.
Newman et al., Saponin adjuvant induction of ovalbumin-specific CD8+ cytotoxic T lymphocyte response. J. Immunol. 1992, 148(8):2357-2362.
Rao & Sung, Saponins as Anticarcinogens, J. Nutr. 1995,125:717S-725S.
Uhlmann et al., Antisense oligonucleotides: A new therapeutic principle. Chem. Rev. 90:544-584, 1990.
Hemmi et al., "A Toll-like receptor recognizes bacterial DNA", Nature, 2000, vol. 408, pp. 740-745.
Liu et al., "QS-22 structure/function studies: effect of acylation on adjuvant activity", Vaccine, , 2002, vol. 20, pp. 2808-2815.
Soltysik et al., "Structure/function studies of QS-21 adjuvant: assessment of triterpene aldehyde and glucuronic acid roles in adjuvant function1", Vaccine, 1995, vol. 13, pp. 1404-1410.
Wagner, "Toll meets bacterial CpG-DNA", Immunity, 2001, vol. 14, pp. 499-502.

Bomford et al., "Adjuvanticity and ISCOM formation by structurally diverse saponins", Vaccine, 1992, vol. 10, pp. 572-577.

Kensil et al., "Novel Adjuvants from *Quillaja saponaria Molina*", Aids Research Review, 1993, vol. 3, pp. 279-389.

Kensil et al., "Separation and Characterization of Saponins with Adjuvant Activity from *Quillaja saponaria Molina* Cortex", Journal of Imm., 1991, vol. 146, No. 2, pp. 431-437.

Klinman, "Therapeutic applications of CpG—containing oligodeoxynucleotides", Antisense and Nucleic Acid Drug Development, 1998, vol. 8, No. 2, pp. 181-184.

Kreig et al., "The role of CpG dinucleotides in DNA vaccines", Trends in Microbiology, 1998, vol. 6, No. 1, pp. 23-27.

So et al., "Effect of a novel saponin adjuvant derived from *Quillaja saponaria* on the immune response to recombinant hepatitis B surface antigen", Molecules and Cells, Apr. 1997, vol. 7, No. 2, pp. 178-186.

Kensil C.R., Saponins as vaccine adjuvants, Critical Reviews in Therapeutic Drug Carrier Systems, 1996, vol. 13, (1-2), pp. 1-55.

Kensil, AIDS Research Rev., 1993, vol. 3, Koff, ed., New York, NY, p. 379-390.

Kensil, J. Immunol., Jan. 15, 1991, vol. 146, No. 2, p. 431-437.

Definition of "explicitly" by Merriam-Webster Online, 2004.

Definition of "chemical modification" by Stedman's Medical Dictionary, 2000.

Chu et al., CpG oligodeoxynucleotides act as adjuvants that switch on T helper 1 (Th1) immunity, J. Exp. Med., 1997, vol. 186, No. 10, pp. 1623-1631.

Weiner et al., Immunostimulatory oligodeoxynucleotides containing the CpG motif are effective as immune adjuvants in tumor antigen immunization, Proc. Natl Acad Sci U.S.A. Sep. 1997, 85(19):7079-7083.

Office Action, dated Oct. 3, 2000, for U.S. Appl. No. 09/369,941.

Response to Restriction Requirement, dated Nov. 7, 2000, for U.S. Appl. No. 09/369,941.

Office Action, dated Jul. 26, 2001, for U.S. Appl. No. 09/369,941.

Office Action, dated Aug. 11, 2004, for U.S. Appl. No. 09/369,941.

Advisory Action, dated Aug. 25, 2005, for U.S. Appl. No. 09/369,941.

\* cited by examiner

Figure 1: CTL Induced by QS-21 and CpG/QS-21

Figure 2: CTL Induced by QS-21 and CpG/QS-21

Figure 3: Antigen-specific Serum IgG1 and IgG2a a divisional of application Ser. No. 09/369,941, filed Aug. 6, 1999, now U.S. Pat. No. 7,049,302 B1, which claims the benefit of U.S. Provisional Application No. 60/128,608, filed Apr. 8, 1999, and of U.S. Provisional Application No. 60/095,913, filed Aug. 10, 1998, the contents of each of which are incorporated herein by reference in their entireties.

FIELD OF THE INVENTION

The present invention is in the field of immune adjuvants and vaccines. The compositions of the invention stimulate immunity, enhance cell-mediated immunity, and enhance antibody production.

BACKGROUND OF THE INVENTION

Adjuvant saponins have been identified and purified from an aqueous extract of the bark of the South American tree, *Quillaja saponaria* Molina. Among the 22 saponin peaks which were separable, the more predominant purified saponins have been identified as QS-7, QS-17, QS-18, and QS-21, also known as QA-7, QA-17, QA-18, and QA-21, respectively. These saponins have been substantially purified by various methods including high pressure liquid chromatography ("HPLC"), low pressure liquid silica chromatography, and hydrophilic interactive chromatography ("HILIC"). The substantially pure saponins have been found to be useful as immune adjuvants for enhancing immune responses in individuals. (Kensil, et al., U.S. Pat. No. 5,057,540; Kensil, et al., *J. Immunol.* 148:2357 (1991); Marciani, et al., *Vaccine* 9:89 (1991).)

Recently, oligonucleotides containing the unmethylated cytosine-guanine ("CpG") dinucleotide in a particular sequence context or motif have been shown to be potent stimulators of several types of immune cells in vitro. (Weiner, et al., *Proc. Natl. Acad. Sci.* 94:10833 (1997).) An immunostimulatory oligonucleotide comprising an unmethylated CpG motif is an dinucleotide within the oligonucleotide that consistently triggers an immunostimulatory response and release of cytokines. CpG motifs can stimulate monocytes, macrophages, and dendritic cells that can produce several cytokines, including the T helper 1 ("Th 1") cytokine interleukin ("IL") 12. (Carson, et al., *J. Exp. Med.* 186:1621 (1997).) This effect causes the induction of IFN-γ secretion by natural killer cells, which in turn, activates macrophages and enhances immunoglobulin isotype switching to IgG2a, a hallmark of T helper cell immunity and differentiation. (Chu, et al., *J. Exp. Med.* 186:1623 (1997).) Klinman, et al., have shown that a DNA motif consisting of an unmethylated CpG dinucleotide flanked by two 5' purines (GpA or ApA) and two 3' pyrimidines (TpC or TpT) optimally stimulated B cells to produce IL-6 and IL-12 and stimulated CD4+ T cells to produce IL-6 and IFN-γ both in vitro and in vivo. (Klinman, et al., *Proc. Natl. Acad. Sci.*, 93:2879 (1996).) Davis, et al., the contents of which are incorporated herein by reference, discovered that nucleic acids containing at least one unmethylated CpG dinucleotide may affect the immune response of a subject (Davis, et al., WO 98/40100, PCT/US98/04703).

SUMMARY OF THE INVENTION

Since immunity plays an important role in the protective response to infection with certain microbial agents, a need exists to characterize other novel adjuvants that may safely induce immunity. Such adjuvants may be potentially incorporated in future human vaccines. Surprisingly, a combination of an oligonucleotide comprising at least one unmethylated CpG dinucleotide and a saponin adjuvant was found to be a powerful stimulator of cell-mediated immunity compared to either adjuvant alone. Antibody titers (antigen-specific) in response to vaccination were significantly higher for vaccines comprising a CpG-containing oligonucleotide/saponin adjuvant combination compared to either saponin or CpG alone and represented a positive synergistic adjuvant effect. Together, these results establish that an immune adjuvant composition comprising an immunostimulatory oligonucleotide comprising at least one unmethylated CpG dinucleotide and a saponin adjuvant is a candidate adjuvant composition for vaccines to induce immunity. Accordingly, the present invention provides novel vaccine compositions which comprise an immunostimulatory oligonucleotide, a saponin adjuvant, and an antigen. Methods for increasing the immune response to an antigen by administrating the inventive vaccine compositions and/or immune adjuvant compositions are other embodiments described herein.

DESCRIPTION OF THE PREFERRED EMBODIMENTS

Figure 1:
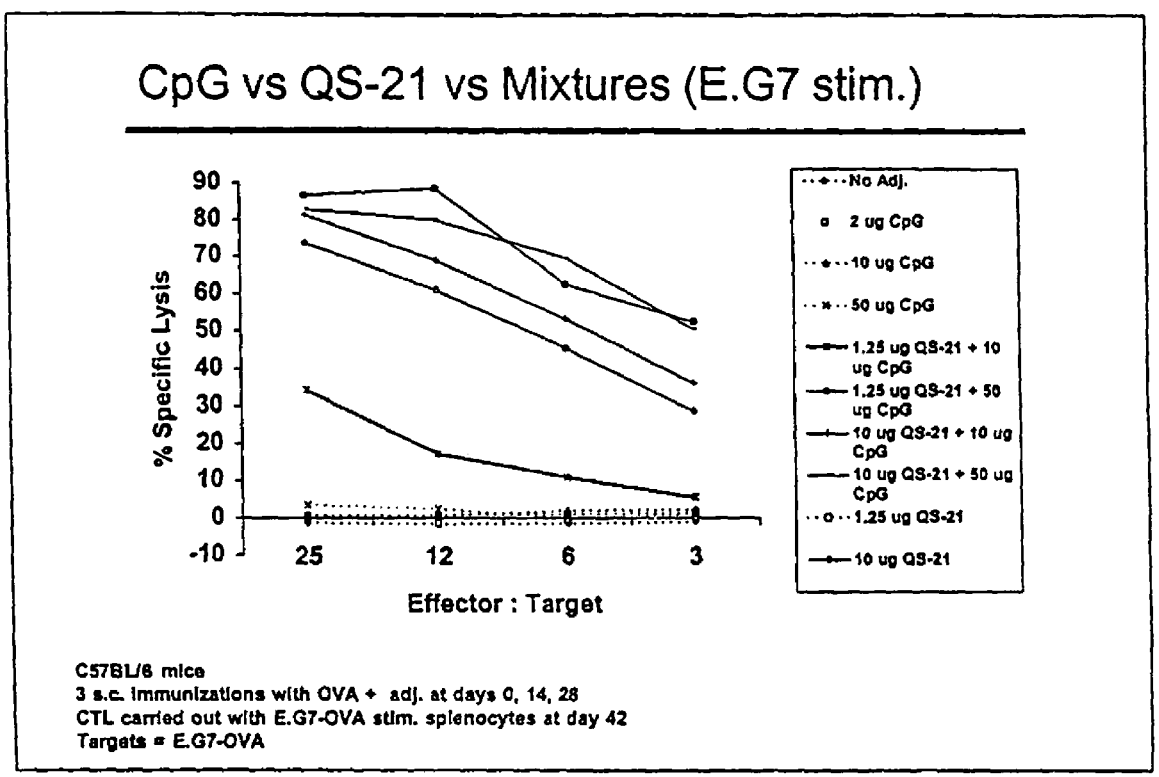
FIG. 1 depicts a graph showing the enhancement of a cell-mediated immune response by QS-21 and CpG oligonucleotide/QS-21 combination, as evidenced by the CTL induction.

The term "saponin" as used herein includes glycosidic triterpenoid compounds which produce foam in aqueous solution, have hemolytic activity in most cases, and possess immune adjuvant activity. The invention encompasses the saponin per se, as well as natural and pharmaceutically acceptable salts and pharmaceutically acceptable derivatives. The term "saponin" also encompasses biologically active fragments thereof.

The saponins of the present invention may be obtained from the tree Quillaja saponaria Molina. (Dalsgaard, Acta Veterinia Scandinavica, 69:1 (1978).) A partially purified saponin enriched extract, prepared as described by Dalsgaard, ("Quil-A") has adjuvant activity. Such an extract can be further separated. Among the 22 saponin peaks which were separable, the more predominant purified saponins have been identified as QS-7, QS-17, QS-18, and QS-21, also known as QA-7, QA-17, QA-18, and QA-21, respectively. (Kensil, et al., U.S. Pat. No. 5,057,540.) These saponins have been substantially purified by various methods including HPLC, low pressure liquid silica chromatography, and HILIC.

As described in Kensil, et al., U.S. Pat. No. 5,057,540, the contents of which are fully incorporated by reference herein, the adjuvant activity of such saponins may be determined by any of a number of methods known to those of ordinary skill in the art. The increase in antibody titer of antibody against specific antigen upon administration of an adjuvant may be used as a criteria for adjuvant activity. (Bomford, Int. Archs. Allergy Appl. Immun. 77:409 (1985).) Briefly, one such test involves injecting CD-1 mice intradermally with an antigen (for instance, i.e., bovine serum albumin, ("BSA")) mixed with varying amounts of the potential adjuvant. Sera was harvested from the mice two weeks later and tested by ELISA for anti-BSA antibody.

Another such test involves injecting inbred mice such as C57BL/6 or Balb/c by subcutaneous route with a protein antigen such as ovalbumin ("OVA") or a polysaccharide antigen such as pneumococcal polysaccharide, mixed with the potential adjuvant. Sera harvested form the mice after one, tow, or three immunizations could be harvested and tested by ELISA for antigen-specific antibody (total immunoglobulin) or for specific mouse IgG subclassses such as IgG1 or IgG2a. Another such test involves injecting C57BL/6 mice with OVA, harvesting spleens after one, two, or three immunizations, stimulating splenocytes with antigen, and then assaying for cytolytic T lymphocyte activity ("killing") of OVA-peptide-expressing target cells. Alternative, a proliferative response could be measured in an in vitro assay by measuring the uptake of $^3$H-thymidine by antigen-stimulated splenocytes obtained from immunized animals.

"QS-21" designates the mixture of components QS-21-V1 and QS-21-V2 which appear as a single peak on reverse phase HPLC on Vydac C4 (5 µm particle size, 300 Å pore, 4.6 mm ID×25 cm length) in 40 mM acetic acid in methanol/water (58/42, v/v). The component fractions are referred to specifically as QS-21-V1 and QS-21-V2 when describing experiments performed on the further purified components.

According to Kensil, et al., U.S. Pat. No. 5,583,112, the contents of which are fully incorporated by reference herein, the carboxyl group on the glucuronic acid of Quillaja saponaria Molina can be conjugated to a protein, a peptide, or a small molecule containing a primary amine. Thus, the present invention relates to a chemically modified saponin adjuvant or a fraction thereof obtainable from a crude Quillaja saponaria Molina extract, wherein the chemically modified saponin or fraction thereof comprises at least one of QS-17, QS-18, QS-21, QS-21-V1, and QS-21-V2, and wherein the modified saponin retains adjuvant activity.

The term "partially pure" means saponins partially separated from compounds normally associated with the saponin in its natural state.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

The present invention may also employ immunostimulatory saponins isolated from other plant species. For example, a saponin from Dolichos lablab has been shown to be useful as an adjuvant (Katayan, et al., Vaccine 17:2733 (1999)).

The term "immunostimulatory oligonucleotide comprising at least one unmethylated CpG dinucleotide" means an oligonucleotide that has been shown to activate the immune system. The immunostimulatory oligonucleotide may, preferably, comprise at least one unmethylated CpG dinucleotide. A "CpG motif" is a stretch of DNA comprising one or more CpG dinucleotides within a specified sequence. The oligonucleotide comprising the CpG motif may be as short as 5-40 base pairs in length. The immunostimulatory oligonucleotide containing the CpG motif may be a monomer or part of a multimer. Alternatively, the CpG motif may be a part of the sequence of a vector that also presents a DNA vaccine. It may be single-stranded or double-stranded. It may be prepared synthetically or produced in large scale in plasmids. One embodiment of the invention covers the immunostimulatory oligonucleotide which contains a CpG motif having the formula 5'$X_1$CG$X_2$3', wherein at least one nucleotide separates consecutive CpGs, and wherein $X_1$ is adenine, guanine, or thymine, and $X_2$ is cytosine, thymine, or adenine. In a preferred embodiment, the CpG motif comprises TCTC-CCAGCGTGCGCCAT (SEQ ID NO:1; also known as "1758") or TCCATGACGTTCCTGACGTT (SEQ ID NO:2; also known as "1826").

DNA containing unmethylated CpG dinucleotide motifs in the context of certain flanking sequences has been found to be a potent stimulator of several types of immune cells in vitro. (Ballas, et al., J. Immunol. 157:1840 (1996); Cowdrey, et al., J. Immunol. 156:4570 (1996); Krieg, et al., Nature 374:546 (1995).) Depending on the flanking sequences, certain CpG motifs may be more immunostimulatory for B cell or T cell responses, and preferentially stimulate certain species. When a humoral response is desired, preferred immunostimulatory oligonucleotides comprising an unmethylated CpG motif will be those that preferentially stimulate a B cell response. When cell-mediated immunity is desired, preferred immunostimulatory oligonucleotides comprising at least one unmethylated CpG dinucleotide will be those that stimulate secretion of cytokines known to facilitate a CD8+ T cell response.

The immunostimulatory oligonucleotides of the invention may be chemically modified in a number of ways in order to stabilize the oligonucleotide against endogenous endonucleases. For example, the oligonucleotides may contain other than phosphodiester linkages in which the nucleotides at the 5' end and/or 3' end of the oligonucleotide have been replaced with any number of non-traditional bases or chemical groups, such as phosphorothioate-modified nucleotides. The immunostimulatory oligonucleotide comprising at least one unmethylated CpG dinucleotide may preferably be modified with at least one such phosphorothioate-modified nucleotide. Oligonucleotides with phosphorothioate-modified linkages may be prepared using methods well known in the field such as phosphoramidite (Agrawal, et al., *Proc. Natl. Acad. Sci.* 85:7079 (1988)) or H-phosphonate (Froehler, et al., *Tetrahedron Lett.* 27:5575 (1986)). Examples of other modifying chemical groups include alkylphosphonates, phosphorodithioates, alkylphosphorothioates, phosphoramidates, 2-O-methyls, carbamates, acetamidates, carboxymethyl esters, carbonates, and phosphate triesters. Oligonucleotides with these linkages can be prepared according to known methods (Goodchild, *Chem. Rev.* 90:543 (1990); Uhlmann, et al., *Chem. Rev.* 90:534 (1990); and Agrawal, et al., *Trends Biotechnol.* 10:152 (1992)).

The term "immune adjuvant" as used herein refers to compounds which, when administered to an individual or tested in vitro, increase the immune response to an antigen in the individual or test system to which the antigen is administered. Preferably, such individuals are mammals, and more preferably, the mammals are humans, however, the invention is not intended to be so limiting. Any animal which may experience the beneficial effects of the vaccines of the invention are within the scope of animals which may be treated according to the claimed invention. Some antigens are weakly immunogenic when administered alone, i.e., inducing no or weak antibody titers or cell-mediated immune response. An immune adjuvant may enhance the immune response of the individual by increasing antibody titers and/or cell-mediated immunity. The adjuvant effect may also lower the dose of the antigen effective to achieve an immune response in the individual.

In a first aspect of the invention, an immune adjuvant composition comprising a saponin adjuvant and an immunostimulatory oligonucleotide may be administered. More preferably, such immune adjuvant composition may increase the immune response to an antigen in an individual or a test system to which the antigen is administered. Preferably, the saponin adjuvant is a saponin from *Quillaja saponaria* Molina. More preferably, the saponin adjuvant is a partially pure or substantially pure saponin from *Quillaja saponaria* Molina. Preferably, the partially pure saponin may comprise QS-7, QS-17, QS-18, and/or QS-21 and may comprise other saponins. Preferably, the substantially pure saponin adjuvant is QS-7, QS-17, QS-18, or QS-21. Most preferably, the substantially pure saponin adjuvant is QS-21. Alternatively, the immune adjuvant composition may comprise more than one substantially pure saponin adjuvant with the immunostimulatory oligonucleotide. In a further preferred embodiment, the saponin adjuvant may cover a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. The immunostimulatory oligonucleotide, preferably, comprises at least one unmethylated CpG dinucleotide. The CpG dinucleotide is preferably a monomer or multimer. Another preferred embodiment of the CpG motif is as a part of the sequence of a vector that also presents a DNA vaccine. Yet another embodiment of the immune adjuvant composition is directed to the immunostimulatory oligonucleotide, wherein the immunostimulatory oligonucleotide is modified. The particular modification may comprise at least one phosphorothioate-modified nucleotide. Further, the immunostimulatory oligonucleotide having at least one unmethylated CpG dinucleotide may comprise a CpG motif having the formula 5'$X_1CGX_2$3', wherein at least one nucleotide separates consecutive CpGs, and wherein $X_1$ is adenine, guanine, or thymine, and $X_2$ is cytosine, thymine, or adenine. The CpG motif may preferentially be TCTCCCAGCGTGCGCCAT or TCCATGACGTTCCTGACGTT.

In a second aspect, the invention is directed to a method for increasing the immune response to an antigen in an individual or a test system to which the antigen is administered comprising administering an effective amount of an immune adjuvant composition comprising a saponin adjuvant and an immunostimulatory oligonucleotide further. Preferably, the saponin adjuvant is a saponin from *Quillaja saponaria* Molina. More preferably, the saponin adjuvant is a partially pure or a substantially pure saponin from *Quillaja saponaria* Molina. The method may also embody an immune adjuvant composition comprising more than one substantially pure saponin adjuvant and immunostimulatory oligonucleotide. The substantially pure saponin adjuvant is preferably QS-7, QS-17, QS-18, or QS-21. Most preferably, the substantially pure saponin adjuvant is QS-21. In a further preferred embodiment, the saponin adjuvant may cover a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. In a preferred embodiment of the method, the immunostimulatory oligonucleotide comprises at least one unmethylated CpG dinucleotide. The CpG motif is preferably a monomer or a multimer. Another preferred embodiment of the method includes the CpG motif as a part of the sequence of a vector that presents a DNA vaccine. Yet another embodiment is directed to the method wherein the immunostimulatory oligonucleotide comprises at least one unmethylated CpG dinucleotide, and wherein furthermore, the immunostimulatory oligonucleotide may be chemically modified to stabilize the oligonucleotide against endogenous endonucleases. The modification may comprise at least one phosphorothioate-modified nucleotide. Further, the method may be directed, in part, to the immunostimulatory oligonucleotide having at least one unmethylated CpG dinucleotide comprising a CpG motif having the formula 5'$X_1CGX_2$3', wherein at least one nucleotide separates consecutive CpGs, and wherein $X_1$ is adenine, guanine, or thymine, and $X_2$ is cytosine, thymine, or adenine. In another preferred method, the unmethylated CpG motif is TCTCCCAGCGTGCGC-CAT or TCCATGACGTTCCTGACGTT.

The term "vaccine composition" herein refers to a composition capable of producing an immune response. A vaccine composition, according to the invention, would produce immunity against disease in individuals. The combination of saponin and immunostimulatory oligonucleotide of the present invention may be administered to an individual to enhance the immune response to any antigen. Preferably, the vaccine composition stimulates immunity. More preferably, the vaccine composition enhances antibody production to an antigen and enhances a cell-mediated immune response to an antigen.

The vaccine composition of the invention may enhance antibody production to an antigen in a positive synergistic manner. The synergistic adjuvant effect of the immunostimulatory oligonucleotide and the saponin adjuvant described herein may be shown in a number of ways. For example, a synergistic adjuvant effect may be demonstrated as an increase in the maximum expected immune response. One may expect an additive effect of combining two adjuvants. Specifically, if one adjuvant, used at optimum doses, produces "X" and the other adjuvant, also used at optimum doses, produces "Y" antibody, then the combination may be expected to produce "X+Y" if the result is additive and not synergistic. A maximum level of response that is considerably higher than "X+Y" would be considered a synergistic effect and would be unexpected. A second indication of synergism would be the appearance of a substantial adjuvant effect at doses that are normally not expected to produce an adjuvant effect. A third indication of synergism would be the appearance of an immune response with earlier kinetics than expected for either adjuvant alone.

Further, typical antigens suitable for the enhanced immune response include antigens derived from any of the following: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, pneumococcus, or tuberculosis; or protozoans, such as *Babeosis bovis* or *Plasmodium*. The antigen may preferably be a protein, a peptide, a polysaccharide, a lipid, a glycolipid, a phospholipid, or a nucleic acid encoding the antigenic protein or peptide of interest. The antigens may be purified from a natural source, synthesized by means of solid phase synthesis, or may be obtained by means of genetic engineering.

Accordingly, in a third aspect, the invention also encompasses a vaccine composition comprising a saponin adjuvant, an immunostimulatory oligonucleotide, and an antigen. The saponin adjuvant may be partially pure or substantially pure saponin from *Quillaja saponaria* Molina. The vaccine compositions may also comprise more than one partially pure or substantially pure saponin adjuvant, an immunostimulatory oligonucleotide further comprising at least one unmethylated CpG motif, and an antigen. Preferably, the partially pure saponin adjuvant comprises QS-7, QS-17, QS-18, and/or QS-21 and may comprise other saponins. Preferably, the substantially pure saponin adjuvant is QS-7, QS-17, QS-18, or QS-21. A further preferred embodiment encompasses saponin adjuvants wherein a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. Most preferably, the partially pure or substantially pure saponin adjuvant in the vaccine composition is QS-21. The immunostimulatory oligonucleotide may preferably comprise at least one unmethylated CpG dinucleotide. The CpG motif may preferably be a monomer or a multimer. Another preferred embodiment of the CpG motif is as a part of the sequence of a vector that also presents a DNA vaccine. Yet another embodiment of the vaccine composition described herein is directed to the immunostimulatory oligonucleotide comprising at least one unmethylated CpG dinucleotide comprises a chemical modification. More particularly, the immunostimulatory oligonucleotide may be modified with at least one phosphorothioate-modified nucleotide. Further, the immunostimulatory oligonucleotide having at least one unmethylated CpG dinucleotide of the vaccine composition comprises a CpG motif having the formula $5'X_1CGX_23'$, wherein at least one nucleotide separates consecutive CpGs, and wherein $X_1$ is adenine, guanine, or thymine, and $X_2$ is cytosine, thymine, or adenine. The unmethylated CpG motif according to this aspect of the invention may preferentially comprise TCTCCCAGCGTGCGCCAT or TCCATGACGTTCCTGACGTT.

A fourth aspect of the invention encompasses a method of stimulating immunity to an antigen in an individual comprising administering an effective amount of a vaccine composition comprising an antigen, a partially pure or substantially pure saponin adjuvant, and an immunostimulatory oligonucleotide. The method also embodies a vaccine composition comprising more than one partially pure or substantially pure saponin adjuvant, an immunostimulatory oligonucleotide, and an antigen. Preferably, the partially pure saponin adjuvant comprises QS-7, QS-17, QS-18, and/or QS-21 and may comprise other saponins. Preferably, the substantially pure saponin adjuvant comprises QS-7, QS-17, QS-18, or QS-21. Most preferably, according to this method, the partially pure or substantially pure saponin adjuvant is QS-21. The saponin adjuvant may preferably be a chemically modified saponin adjuvant or a fraction thereof obtainable from a crude *Quillaja saponaria* Molina extract, wherein the chemically modified saponin or fraction thereof comprises at least one of QS-17, QS-18, QS-21, QS-21-V1, and QS-21-V2, and wherein the chemically modified saponin retains adjuvant activity. Preferably, the method comprises administering an immunostimulatory oligonucleotide which further comprises at least one unmethylated CpG dinucleotide. The CpG dinucleotide therein is a monomer or a multimer. Another preferred embodiment of the method includes the CpG motif as a part of the sequence of a vector that also presents a DNA vaccine. Yet another embodiment of the method disclosed herein is directed to the immunostimulatory oligonucleotide comprising at least one unmethylated CpG dinucleotide, wherein the immunostimulatory oligonucleotide may be chemically modified to increase its stability to endogenous endonucleases. Such a modification may comprise at least one phosphorothioate-modified nucleotide. Further, the immunostimulatory oligonucleotide having at least one unmethylated CpG dinucleotide may comprise a CpG motif having the formula $5'X_1CGX_23'$, wherein at least one nucleotide separates consecutive CpGs, and wherein $X_1$ is adenine, guanine, or thymine, and $X_2$ is cytosine, thymine, or adenine. In another preferred embodiment, the unmethylated CpG motif is TCTCCCAGCGTGCGCCAT or TCCATGACGTTCCTGACGTT.

Other useful methods for the vaccine composition include enhancing antibody production to an antigen and enhancing cell-mediated immunity. More preferably, the vaccine composition enhances antibody production to an antigen and enhances a cell-mediated immunity. Most preferably, the vaccine composition enhances antibody production to an antigen in a positive synergistic manner.

Administration of the compositions of the present invention may be by parenteral, intravenous, intramuscular, subcutaneous, intranasal, oral, mucosal, or any other suitable means. The dosage administered may be dependent upon the age, weight, kind of concurrent treatment, if any, and nature of the antigen administered. The initial dose may be followed up with a booster dosage after a period of about four weeks to enhance the immunogenic response. Further booster dosages may also be administered. The composition may be given as a single injection of a mixed formulation of saponin, oligonucleotide, and antigen or as separate injections given at the same site within a short period of time (i.e., 0-2 days).

The effective compositions of the present invention may be employed in such forms as capsules, liquid solutions, suspensions or elixirs for oral administration, or sterile liquid forms such as solutions or suspensions. Any inert acceptable carrier may preferably be used, such as saline, or PBS, or any such acceptable carrier in which the compositions of the present invention have suitable solubility properties for use of the present invention.

EXAMPLES

A well-established animal model was used to assess whether formulations of CpG oligonucleotide and QS-21 together could function as an immune adjuvant. In brief, experiments were set up to compare QS-21 to the recently reported adjuvant CpG motif. A CpG sequence (e.g., 1758), reported to serve as an adjuvant for a B-cell lymphoma idiotype-KLH vaccine in mice, was selected. One experiment evaluated whether the CpG motif, alone or in combination with QS-21, can serve as an adjuvant for a subunit vaccine, e.g., OVA, in mice in inducing CTL responses. This work included a dose range experiment with CpG to determine the optimum dose.

In addition to comparing CpG and QS-21 as adjuvants, a second experiment combining CpG oligonucleotide with suboptimal doses of QS-21 (e.g., 1.25 μg) was conducted to assess whether CpG oligonucleotide can affect the adjuvant effect of QS-21.

Also, an experiment was performed to determine whether the CpG and QS-21 combination could enhance antibody production, specifically the isotype profile of a antigen-specific antibody response.

Finally, a series of experiments were performed to determine whether a combination of CpG oligonucleotide and saponin would enhance antibody production in a positive synergistic manner. This work used vaccine formulations of pneumococcal Type 14 polysaccharide and QS-21 and CpG oligonucleotide and evaluated specific antibody titers harvested from mice on days 21 and 42 after immunization on days 0 and 28. Another CPG sequence (e.g., 1826), reported to serve as an adjuvant for hen egg lysozyme in mice, was selected.

The experiments were done using materials from the following suppliers: OVA, Grade VI (Sigma); pneumococcal Type 14 polysaccharide (ATCC); QS-21 (Aquila); CpG oligonucleotides included the phosphorothioate-modified sequence 1758 TCTCCCAGCGTGCGCCAT and phosphorothioate-modified sequence 1826 TCCATGACGTTCCTGACGTT (Life Technologies (Gibco)).

Example 1

CTL Induced by QS-21 and CpG/QS-21

C57BL/6 mice (5 per group, female, 8-10 weeks of age) were immunized by subcutaneous route at days 1, 15, and 29. The vaccines were 25 μg OVA antigen plus the indicated doses of adjuvant in a total volume of 0.2 ml phosphate-buffered saline. The CpG motif used in this experiment was a phosphorothioate-modified oligonucleotide 1758 with a sequence of TCTCCCAGCGTGCGCCAT (Weiner, et al., *Proc. Natl. Acad. Sci.* 94:10833 (1997).) Splenocytes were removed at day 42 for use as effector cells in the CTL assay. They were stimulated in vitro for 6 days with mitomycin C-treated E.G7-OVA cells and then used in a standard $^{51}$CR release CTL assay. E.G7-OVA cells (loaded with $^{51}$CR) were used as target cells. The background lysis of EL4 cells (not transfected by OVA) was subtracted from the lysis of E.G7-OVA cells to obtain a percent (%) antigen-specific lysis.

The results, as shown in FIG. 1, indicate that no lysis was observed in the absence of adjuvant, with any CpG dose, or with 1.25 μg of QS-21 (suboptimal dose). However, the suboptimal dose of QS-21, in combination with CpG, induced significant CTL. The results show a substantial adjuvant effect at doses that are normally not expected to produce such an adjuvant effect. This positive synergistic effect was most notable at the higher dose of CpG (50 μg). The adjuvant effect was comparable to that achieved with the optimal 10 μg QS-21 control.

Example 2

CTL Induced by QS-21 and CpG/QS-21

Splenocytes from mice immunized as described in FIG. 1 were used in a CTL assay. Splenocytes were stimulated in vitro with denatured OVA for six days prior to use in the CTL assay. The assay was carried out against E.G7-OVA cells as described in Example 1.

Figure 2:
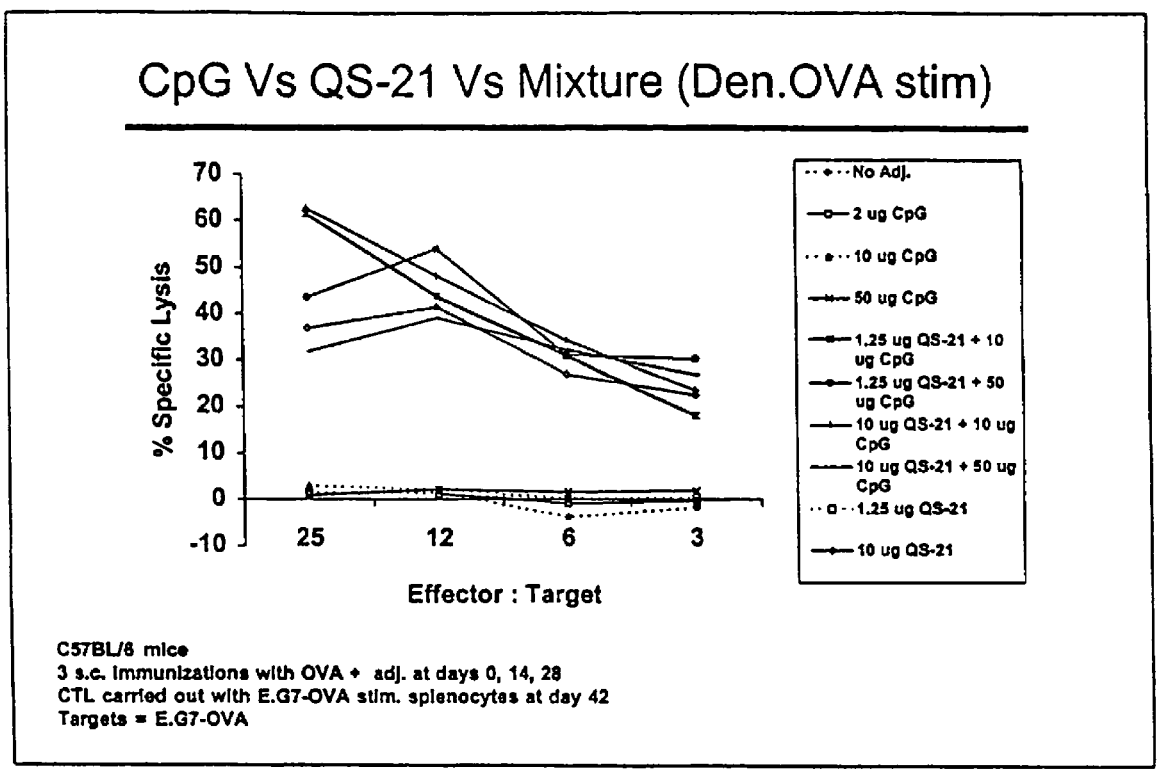
FIG. 2 provides a graph showing the enhancement of a cell-mediated immune response by QS-21 and CpG oligonucleotide/QS-21 combination, as evidenced by the CTL induction.

As evident from the results in FIG. 2, no lysis was observed in the absence of adjuvant, with any CpG dose, or with 1.25 μg of QS-21 (suboptimal dose). However, the suboptimal dose of QS-21, in combination with CpG, induced significant CTL (comparable to the optimal 10 μg QS-21 control). The results illustrate the positive synergism between the CpG and the QS-21 that was unexpected at a suboptimal dose.

Example 3

Antigen-Specific Serum IgG1 and IgG2a

Figure 3:
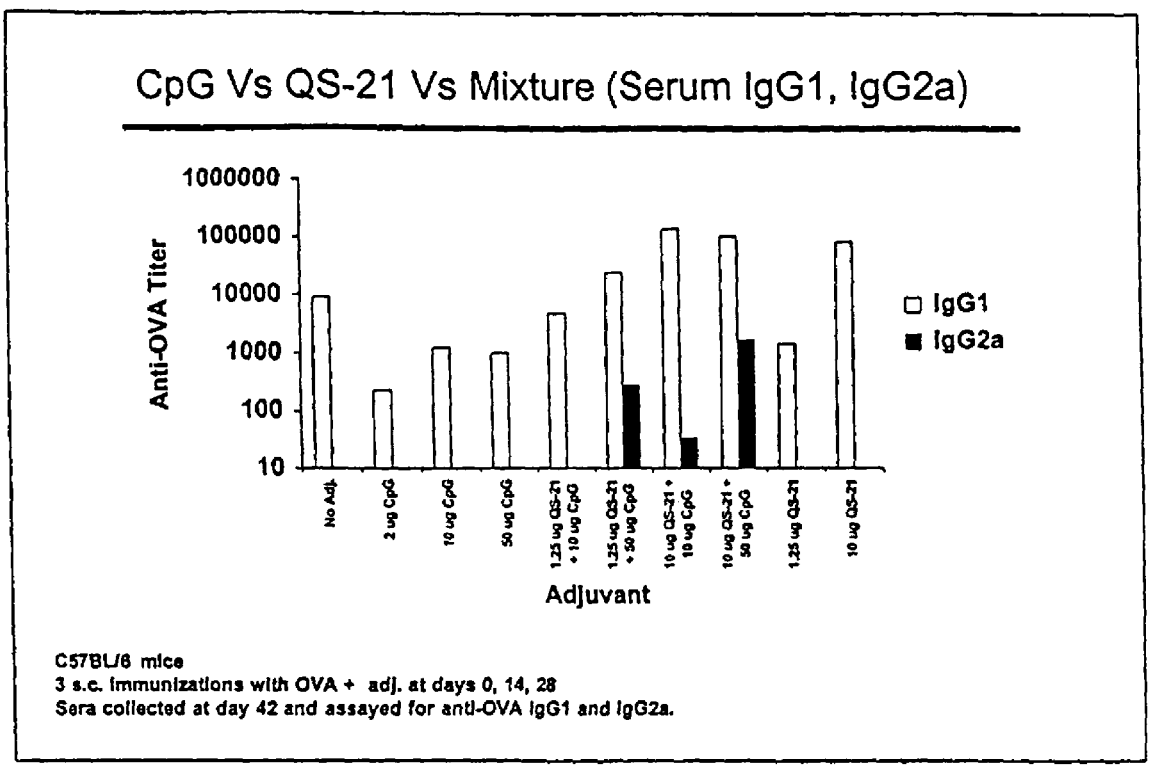
FIG. 3 shows a bar graph of enhanced antibody production, particularly the antibody subclasses such as IgG2a that are influenced by Th 1 cytokines.

Serum titers to OVA were determined by EIA on sera collected on day 42 from the mice immunized as described in Example 1. IgG subclass IgG1 and IgG2a titers were determined for individual mice (5 mice per group) and are plotted as a geometric mean titer. The IgG1 titers were highest in groups receiving QS-21 alone (at the 10 μg dose) or 10 μg QS-21 in combination with either 10 or 50 μg (approximate 10 fold enhancement over the unadjuvanted group) as seen in FIG. 3. The IgG2a response was not detectable in any groups except for the combination of 10 μg QS-21 (optimal dose) with 10 or 50 μg CpG and the combination of 1.25 μg QS-21 (suboptimal dose) with 50 μg CpG. IgG2a was not detected with any CpG dose used alone, with any QS-21 dose used alone, or in the unadjuvanted group.

Example 4

Antibody Induced by OS-21 and OS-21/CpG to Pneumococcal Polysaccharide Antigen

BALB/c mice (5 mice per group, female, 8-10 weeks of age) were immunized by subcutaneous route at day 0 only or at days 0 and 28. The vaccines were 0.5 μg pneumococcal Type 14 polysaccharide plus the indicated doses of adjuvant in a total volume of 0.2 ml phosphate-buffered saline. The immunostimulatory motif CpG used in this experiment was a phosphorothioate-modified oligonucleotide 1826 with a sequence of TCCATGACGTTCCTGACGTT (Chu, et al., *J. Exp. Med.* 186:1623-1631 (1997)). QS-21 was used at a dose of 1.25 μg or 10 μg. CpG ODN 1826 was used at a dose of only 10 μg.

Sera from mice receiving a single immunization was collected at day 21. Sera from mice receiving 2 immunizations was collected at day 42. Antibody titers specific for Type 14 polysaccharide was determined on the sera. IgG subclasses IgG1, IgG2a, and IgG3 were determined for an equivolume sera pool from the mice in each group. After a single immunization, IgG1 titers were 66 fold higher for the 10 μg QS-21/

Figure 4:
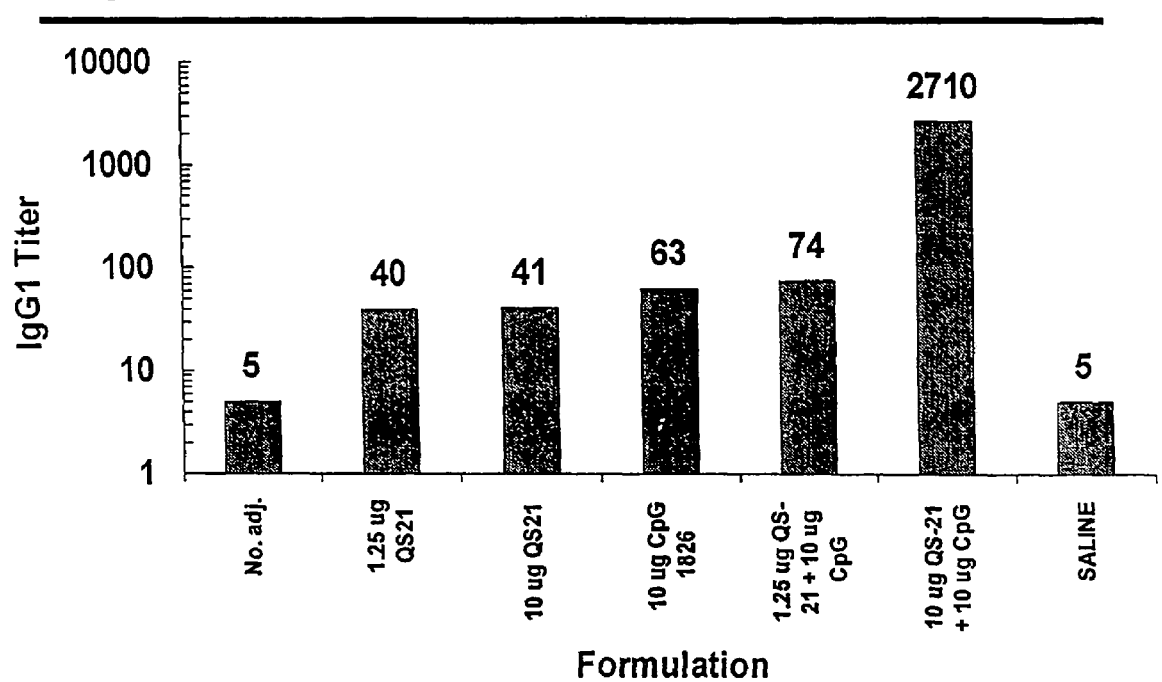
FIG. 4 shows a bar graph of IgG1 titers specific for pneumococcal Type 14 polysaccharide with the various formulations and for combinations of QS-21 and CpG oligonucleotide in mouse sera collected 21 days after a first immunization given on day 0.
Figure 5:
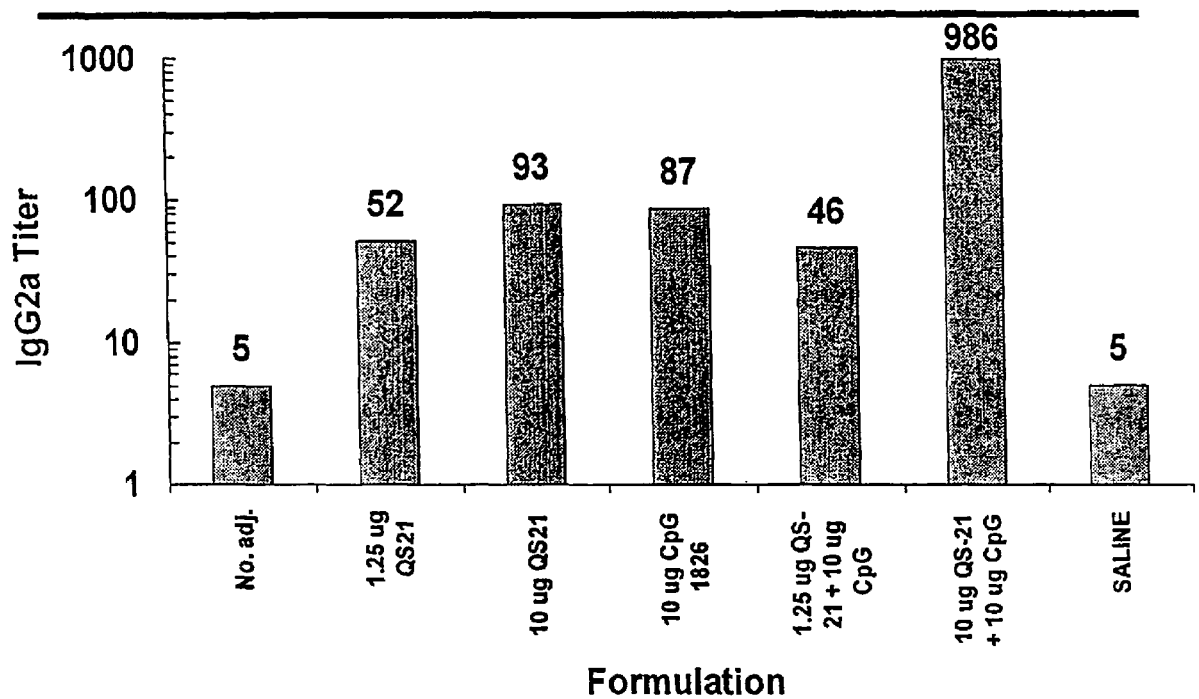
FIG. 5 illustrates a bar graph of IgG2a titers specific for pneumococcal Type 14 polysaccharide with the various formulations and/or combinations of QS-21 and CpG oligonucleotide in mouse sera collected 21 days after a first immunization given on day 0.
Figure 6:
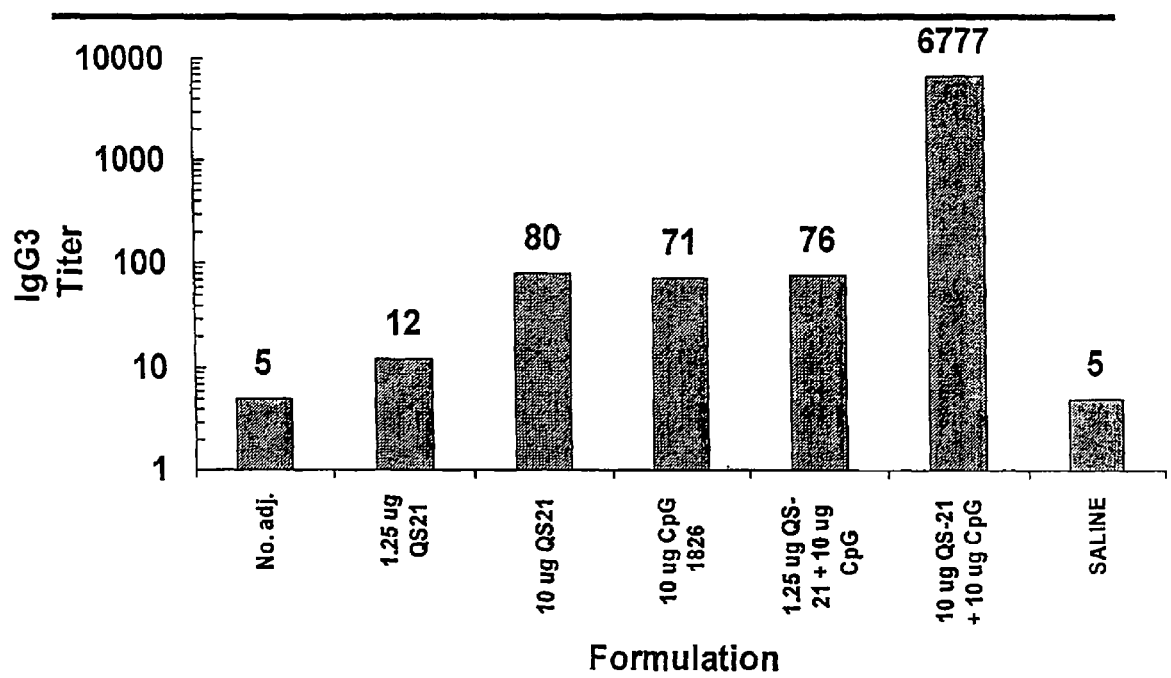
FIG. 6 provides a bar graph of IgG3 titers specific for pneumococcal Type 14 polysaccharide with the various formulations and/or combinations of QS-21 and CpG oligonucleotide in mouse sera collected 21 days after a first immunization given on day 0.

10 µg CpG combination than for QS-21 alone and were 43 fold higher than for CpG alone (FIG. 4). IgG2a titers were 11 fold higher for the 10 µg QS-21/CpG combination than for either QS-21 alone or CpG alone (FIG. 5). IgG3 titers were 85 fold higher for the 10 µg QS-21/CpG combination than for QS-21 alone and were 95 fold higher than for CpG alone (FIG. 6).

Figure 7:
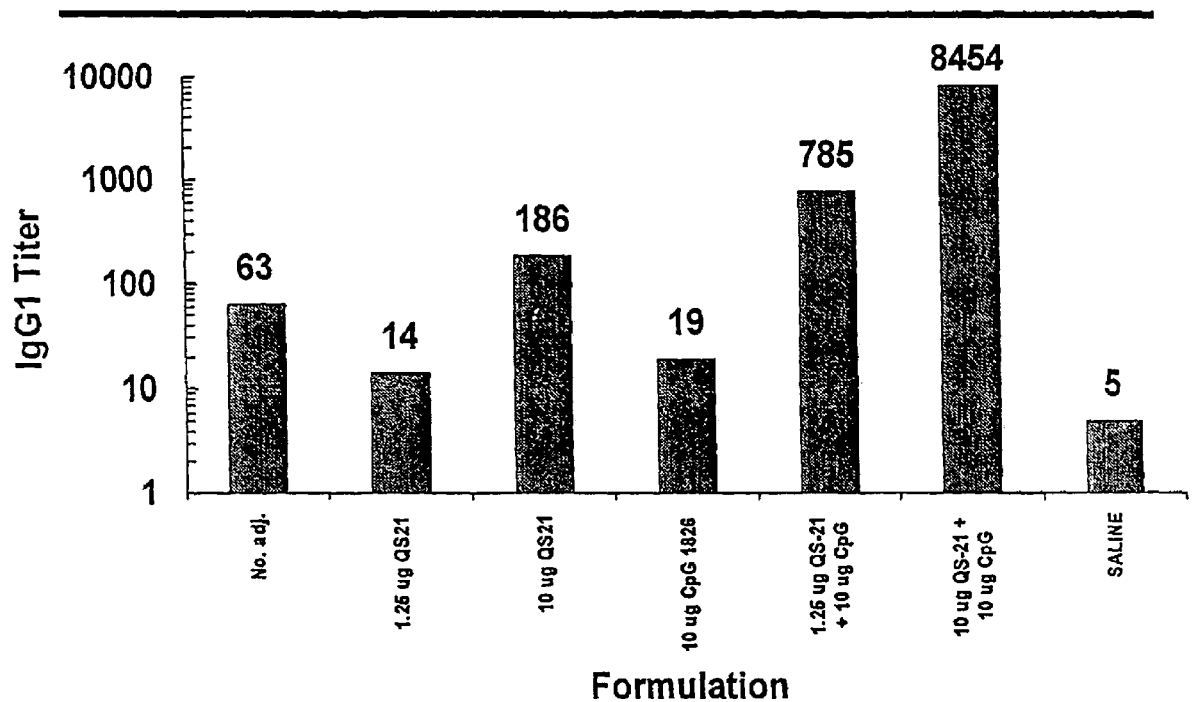
FIG. 7 depicts a bar graph of IgG1 titers specific for pneumococcal Type 14 polysaccharide with the various formulations and/or combinations of QS-21 and CpG oligonucleotide in mouse sera collected 14 days after a second immunization given 28 days after the first immunization.
Figure 8:
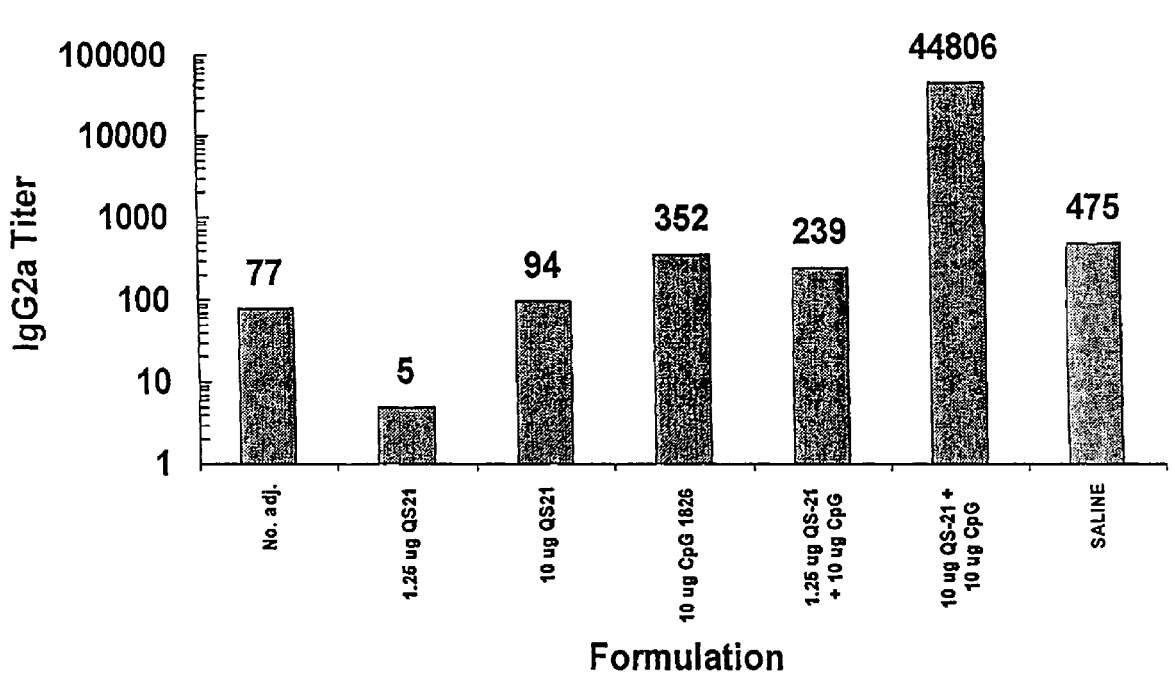
FIG. 8 provides a bar graph of IgG2a titers specific for pneumococcal Type 14 polysaccharide with the various formulations and/or combinations of QS-21 and CpG oligonucleotide in mouse sera collected 14 days after a second immunization given 28 days after the first immunization.
Figure 9:
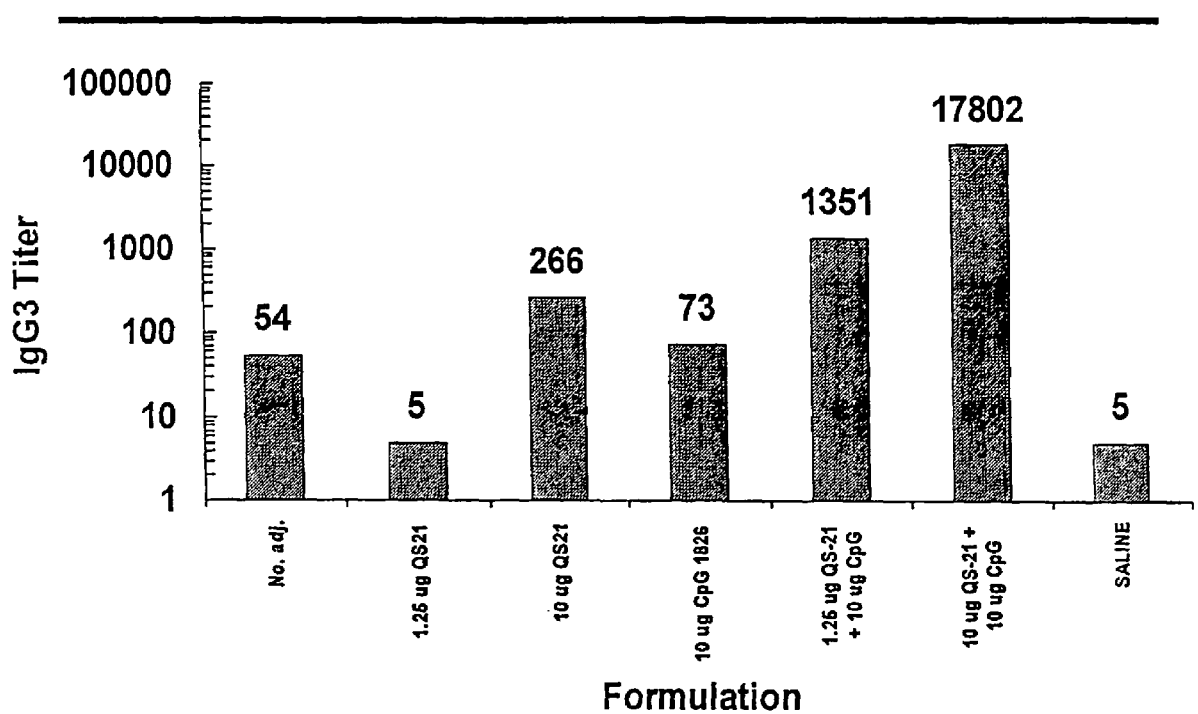
FIG. 9 shows a bar graph of IgG3 titers specific for pneumococcal Type 14 polysaccharide with the various formulations and/or combinations of QS-21 and CpG oligonucleotide in mouse sera collected 14 days after a second immunization given 28 days after the first immunization.

After two immunizations, IgG1 titers were 46 fold higher for the 10 µg QS-21/CpG combination than for QS-21 alone and were 444 fold higher than for CpG alone (FIG. 7). IgG2a titers were 476 fold higher for the 10 µg QS-21/CpG combination than for QS-21 alone and were 127 fold higher than for CpG alone (FIG. 5). IgG3 titers were 67 fold higher for the 10 µg QS-21/CpG combination than for QS-21 alone and were 243 fold higher than for CpG alone (FIG. 9). The enhancement of these titers shows that this is a positive synergistic effect and is not simply an additive adjuvant effect of combining these two adjuvants. In addition, the combination of low doses of QS-21 (1.25 µg) with 10 µg CpG also produced IgG1 and IgG3 titers after two immunizations that were higher than those produced by either 1.25 µg QS-21 alone, 10 µg QS-21 alone, or 10 µg CpG alone.

The invention now being fully described, it will be apparent to one of ordinary skill in the art that many changes and modifications can be made thereto without departing from the spirit or scope of the invention as set forth below.

I claim:

1. A vaccine composition comprising:
   (a) an antigen;
   (b) a *Quillaja saponaria* saponin possessing immune adjuvant activity; and
   (c) an immunostimulatory oligonucleotide comprising at least one unmethylated CpG dinucleotide, wherein the immunostimulatory oligonucleotide is not a part of a DNA vaccine vector,
   wherein the saponin and immunostimulatory oligonucleotide have a synergistic adjuvant effect.

2. The vaccine composition as claimed in claim 1, wherein the saponin comprises a substantially pure saponin.

3. The vaccine composition as claimed in claim 2, wherein the substantially pure saponin is QS-7, QS-17, QS-18, or QS-21.

4. The vaccine composition as claimed in claim 3, wherein the substantially pure saponin is QS-21.

5. The vaccine composition as claimed in claim 1, wherein the immunostimulatory oligonucleotide is modified.

6. The vaccine composition as claimed in claim 1, wherein the immunostimulatory oligonucleotide is modified with at least one phosphorothioate-modified nucleotide.

7. The vaccine composition as claimed in claim 1, wherein the immunostimulatory oligonucleotide comprises a CpG motif having the formula 5'$X_1$CG$X_2$3', wherein at least one nucleotide separates consecutive CpGs, and wherein $X_1$ is adenine, guanine, or thymine, and $X_2$ is cytosine, thymine, or adenine.

8. The vaccine composition as claimed in claim 7, wherein the CpG motif comprises TCTCCCAGCGTGCGCCAT (SEQ ID NO:1) or TCCATGACGTTCCTGACGTT (SEQ ID NO:2).

9. The vaccine composition as claimed in any one of claims 1 and 3-5, wherein the composition increases or induces an immune response to the antigen relative to the immune response to the antigen in the absence of said saponin and said immunostimulatory oligonucleotide when administered to a mammal.

10. The vaccine composition as claimed in any one of claims 1 and 3-5, wherein the composition increases or induces an immune response to the antigen relative to the immune response to the antigen in the absence of said saponin and said immunostimulatory oligonucleotide when administered to a human.

11. The vaccine composition as claimed in claim 1, wherein the composition enhances antibody production to the antigen relative to the antibody production to the antigen in the absence of said saponin and immunostimulatory oligonucleotide.

12. The vaccine composition as claimed in claim 11, wherein the composition enhances antibody production to the antigen in a positive synergistic manner.

13. The vaccine composition as claimed in claim 1, wherein the composition enhances cell-mediated immunity to the antigen relative to the cell-mediated immunity to the antigen in the absence of said saponin and immunostimulatory oligonucleotide.

14. The vaccine composition as claimed in claim 1, wherein the antigen comprises a protein, a peptide, a polysaccharide, a lipid, a glycolipid, or a phospholipid.

15. A method for stimulating immunity to an antigen in an individual comprising administering to said individual an effective amount of a vaccine composition as claimed in claim 1.

16. The method as claimed in claim 15, wherein the saponin comprises a substantially pure saponin.

17. The method as claimed in claim 16, wherein the substantially pure saponin is QS-7, QS-17, QS-18, or QS-21.

18. The method as claimed in claim 16, wherein the substantially pure saponin is QS-21.

19. The method as claimed in claim 15, wherein the immunostimulatory oligonucleotide is modified.

20. The method as claimed in claim 19, wherein the immunostimulatory oligonucleotide is modified with at least one phosphorothioate-modified nucleotide.

21. The method as claimed in claim 15, wherein the immunostimulatory oligonucleotide comprises a CpG motif having the formula 5'$X_1$CG$X_2$3', wherein at least one nucleotide separates consecutive CpGs, and wherein $X_1$ is adenine, guanine, or thymine, and $X_2$ is cytosine, thymine, or adenine.

22. The method as claimed in claim 21, wherein the CpG motif comprises TCTCCCAGCGTGCGCCAT (SEQ ID NO:1) or TCCATGACGTTCCTGACGTT (SEQ ID NO:2).

23. The method as claimed in claim 15, wherein the composition increases or induces an immune response to the antigen relative to the immune response to the antigen in the absence of said saponin and said immunostimulatory oligonucleotide when administered to a mammal.

24. The method as claimed in claim 15, wherein the composition increases or induces an immune response to the antigen relative to the immune response to the antigen in the absence of said saponin and said immunostimulatory oligonucleotide when administered to a human.

25. The method as claimed in claim 15, wherein the composition increases or induces an immune response to the antigen relative to the immune response to the antigen in the absence of said saponin and said immunostimulatory oligonucleotide when administered to an animal.

26. The method as claimed in claim 15, wherein the method further enhances antibody production to the antigen relative to the antibody production to the antigen in the absence of said saponin and immunostimulatory oligonucleotide.

27. The method as claimed in claim 26, wherein the method further enhances antibody production to the antigen in a positive synergistic manner.

28. The method as claimed in claim 15, wherein the method further enhances cell-mediated immunity to the antigen relative to the cell-mediated immunity to the antigen in the absence of said saponin and immunostimulatory oligonucleotide.

29. The method as claimed in claim 15, wherein the antigen comprises a protein, a peptide, a polysaccharide, a lipid, a glycolipid, or a phospholipid.

30. The vaccine composition as claimed in claim 1, wherein the immunostimulatory oligonucleotide is 5-40 bases in length.

31. The vaccine composition as claimed in claim 5, wherein the composition increases or induces an immune response to the antigen relative to the immune response to the antigen in the absence of said saponin and said immunostimulatory oligonucleotide when administered to a mammal.

32. The vaccine composition as claimed in claim 5, wherein the composition increases or induces an immune response to the antigen relative to the immune response to the antigen in the absence of said saponin and said immunostimulatory oligonucleotide when administered to a human.

33. The vaccine composition as claimed in claim 14, wherein the antigen comprises a protein or a peptide.

34. The vaccine composition as claimed in claim 1, wherein the saponin is Quil-A.

35. The vaccine composition as claimed in claim 1, wherein the composition stimulates cell-mediated immunity in a positive synergistic manner.

36. The method as claimed in claim 29, wherein the antigen comprises a protein or a peptide.

37. A vaccine composition comprising:
(a) an antigen;
(b) a *Quillaja saponaria* saponin possessing immune adjuvant activity; and
(c) an immunostimulatory oligonucleotide comprising at least one unmethylated CpG dinucleotide,
wherein the saponin is substantially pure, and the saponin is QS-7, QS-17, QS-18 or QS-21, and wherein the saponin and immunostimulatory oligonucleotide have a synergistic adjuvant effect.

38. The vaccine composition as claimed in claim 37, wherein the substantially pure saponin is QS-21.

39. The vaccine composition as claimed in claim 37 or 38, wherein the immunostimulatory oligonucleotide comprises at least one chemical group selected from the group consisting of phosphorothioate, alkylphosphonate, phosphorodithioate, alkylphosphorothioate, phosphoramidate, 2-O-methyl, carbamate, acetamidate, carboxymethyl ester, carbonate, and phosphate triester.

40. A vaccine composition comprising:
(a) an antigen;
(b) a *Quillaja saponaria* saponin possessing immune adjuvant activity; and
(c) an immunostimulatory oligonucleotide comprising at least one unmethylated CpG dinucleotide,
wherein the immunostimulatory oligonucleotide comprises at least one chemical group selected from the group consisting of phosphorothioate, alkylphosphonate, phosphorodithioate, alkylphosphorothioate, phosphoramidate, 2-O-methyl, carbamate, acetamidate, carboxymethyl ester, carbonate, and phosphate triester, and wherein the saponin and immunostimulatory oligonucleotide have a synergistic adjuvant effect.

41. The vaccine composition as claimed in claim 40, wherein the immunostimulatory oligonucleotide comprises TCTCCCAGCGTGCGCCAT (SEQ ID NO:1) or TCCATGACGTTCCTGACGTT (SEQ ID NO:2).

42. A vaccine composition comprising:
(a) an antigen;
(b) a *Quillaja saponaria* saponin possessing immune adjuvant activity; and
(c) an immunostimulatory oligonucleotide comprising at least one unmethylated CpG dinucleotide,
wherein the immunostimulatory oligonucleotide comprises TCTCCCAGCGTGCGCCAT (SEQ ID NO:1), and wherein the saponin and immunostimulatory oligonucleotide have a synergistic adjuvant effect.

43. The vaccine composition as claimed in claim 42, wherein the saponin is substantially pure, and the saponin is QS-7, QS-17, QS-18 or QS-21.

44. The vaccine composition as claimed in claim 43, wherein the substantially pure saponin is QS-21.

45. The vaccine composition as claimed in any one of claims 42-44, wherein the immunostimulatory oligonucleotide comprises at least one chemical group selected from the group consisting of phosphorothioate, alkylphosphonate, phosphorodithioate, alkylphosphorothioate, phosphoramidate, 2-O-methyl, carbamate, acetamidate, carboxymethyl ester, carbonate, and phosphate triester.

46. A vaccine composition comprising:
    (a) an antigen;
    (b) a *Quillaja saponaria* saponin possessing immune adjuvant activity; and
    (c) an immunostimulatory oligonucleotide comprising at least one unmethylated CpG dinucleotide,
    wherein the immunostimulatory oligonucleotide comprises TCCATGACGTTCCTGACGTT (SEQ ID NO:2), and wherein the saponin and immunostimulatory oligonucleotide have a synergistic adjuvant effect.

47. The vaccine composition as claimed in claim 46, wherein the saponin is substantially pure, and the saponin is QS-7, QS-17, QS-18 or QS-21.

48. The vaccine composition as claimed in claim 47, wherein the substantially pure saponin is QS-21.

49. The vaccine composition as claimed in any one of claims 46-48, wherein the immunostimulatory oligonucleotide comprises at least one chemical group selected from the group consisting of phosphorothioate, alkylphosphonate, phosphorodithioate, alkylphosphorothioate, phosphoramidate, 2-O-methyl, carbamate, acetamidate, carboxymethyl ester, carbonate, and phosphate triester.

50. A vaccine composition comprising:
    (a) an antigen;
    (b) a *Quillaja saponaria* saponin possessing immune adjuvant activity; and
    (c) an immunostimulatory oligonucleotide
    comprising at least one unmethylated CpG dinucleotide, wherein the immunostimulatory oligonucleotide is 5-40 bases in length, and wherein the saponin and immunostimulatory oligonucleotide have a synergistic adjuvant effect.

51. The vaccine composition as claimed in claim 50, wherein the saponin is substantially pure, and the saponin is QS-7, QS-17, QS-18 or QS-21.

52. The vaccine composition as claimed in claim 51, wherein the substantially pure saponin is QS-21.

53. The vaccine composition as claimed in any one of claims 50-52, wherein the immunostimulatory oligonucleotide comprises at least one chemical group selected from the group consisting of phosphorothioate, alkylphosphonate, phosphorodithioate, alkylphosphorothioate, phosphoramidate, 2-O-methyl, carbamate, acetamidate, carboxymethyl ester, carbonate, and phosphate triester.

54. The vaccine composition as claimed in claim 50, wherein the immunostimulatory oligonucleotide comprises TCTCCCAGCGTGCGCCAT (SEQ ID NO:1) or TCCATGACGTTCCTGACGTT (SEQ ID NO:2).

55. A vaccine composition comprising:
    (a) an antigen;
    (b) a *Quillaja saponaria* saponin possessing immune adjuvant activity, wherein the saponin is a chemically modified saponin; and
    (c) an immunostimulatory oligonucleotide comprising at least one unmethylated CpG dinucleotide,
    wherein the saponin and immunostimulatory oligonucleotide have a synergistic adjuvant effect.

56. The vaccine composition as claimed in claim 55, wherein the saponin is substantially pure, and the saponin is a chemically modified QS-7, QS-17, QS-18 or QS-21.

57. The vaccine composition as claimed in claim 56, wherein the substantially pure saponin is a chemically modified QS-21.

58. The vaccine composition as claimed in any one of claims 55-57, wherein the immunostimulatory oligonucleotide comprises at least one chemical group selected from the group consisting of phosphorothioate, alkylphosphonate, phosphorodithioate, alkylphosphorothioate, phosphoramidate, 2-O-methyl, carbamate, acetamidate, carboxymethyl ester, carbonate, and phosphate triester.

59. The vaccine composition as claimed in claim 55, wherein the immunostimulatory oligonucleotide comprises TCTCCCAGCGTGCGCCAT (SEQ ID NO:1) or TCCATGACGTTCCTGACGTT (SEQ ID NO:2).

60. The vaccine composition as claimed in claim 1, wherein the saponin is a chemically modified saponin.

61. The vaccine composition as claimed in claim 1 formulated for parenteral, intravenous, intramuscular, or subcutaneous administration.

62. The vaccine composition as claimed in any one of claim 1, 37, 40, 42, 46, 50, or 55, wherein the antigen is derived from a virus.

63. The vaccine composition as claimed in any one of claim 1, 37, 40, 42, 46, 50, or 55, wherein the antigen is derived from a bacterium.

64. The vaccine composition as claimed in any one of claim 1, 37, 40, 42, 46, 50, or 55, wherein the antigen is derived from a protozoan.

65. The vaccine composition as claimed in claim 64, wherein the protozoan is *Plasmodium*.

\* \* \* \* \*

UNITED STATES PATENT AND TRADEMARK OFFICE
CERTIFICATE OF CORRECTION

Page 1 of 1

PATENT NO. : 7,858,589 B2
APPLICATION NO. : 11/373806
DATED : December 28, 2010
INVENTOR(S) : Charlotte A. Kensil It is certified that error appears in the above-identified patent and that said Letters Patent is hereby corrected as shown below:

Col. 12 in Claim 9, line 19, "3-5" should read --2-4--

Col. 12 in Claim 10, line 25, "3-5" should read --2-4--

Col. 13 in Claim 18, line 12, "16" should read --17--

Signed and Sealed this
Twelfth Day of April, 2011

David J. Kappos
*Director of the United States Patent and Trademark Office*

SEQUENCE LISTING

```
<160> NUMBER OF SEQ ID NOS: 2

<210> SEQ ID NO 1
<211> LENGTH: 18
<212> TYPE: DNA
<213> ORGANISM: Quillaja saponaria

<400> SEQUENCE: 1
tctcccagcg tgcgccat                                                 18

<210> SEQ ID NO 2
<211> LENGTH: 20
<212> TYPE: DNA
<213> ORGANISM: Quillaja saponaria

<400> SEQUENCE: 2
tccatgacgt tcctgacgtt                                               20
```